(12) United States Patent
McNeely

(10) Patent No.: US 11,426,699 B2
(45) Date of Patent: Aug. 30, 2022

(54) CAPILLARY PRESSURE RE-SET MECHANISM AND APPLICATIONS

(71) Applicant: GattaCo Inc., Murrieta, CA (US)

(72) Inventor: Michael Ryan McNeely, Murrieta, CA (US)

(73) Assignee: GattaCo Inc., Murrieta, CA (US)

( * ) Notice: Subject to any disclaimer, the term of this patent is extended or adjusted under 35 U.S.C. 154(b) by 28 days.

(21) Appl. No.: 17/126,322

(22) Filed: Dec. 18, 2020

(65) Prior Publication Data

US 2021/0229041 A1    Jul. 29, 2021

Related U.S. Application Data

(60) Continuation of application No. 16/513,518, filed on Jul. 16, 2019, now Pat. No. 10,870,085, which is a division of application No. 15/312,311, filed as application No. PCT/US2015/034608 on Jun. 7, 2015, now Pat. No. 10,532,325.

(60) Provisional application No. 62/011,661, filed on Jun. 13, 2014.

(51) Int. Cl.
*B01D 63/08*     (2006.01)
*G01N 33/49*     (2006.01)

(52) U.S. Cl.
CPC ......... *B01D 63/087* (2013.01); *G01N 33/491* (2013.01)

(58) Field of Classification Search
CPC .... B01D 63/028; B01D 63/087; B01D 61/18; G01N 33/491
See application file for complete search history.

*Primary Examiner* — Bradley R Spies
(74) *Attorney, Agent, or Firm* — Schwegman Lundberg & Woessner, P.A.

(57) ABSTRACT

Many hand-held diagnostics are limited in their functionality due to the challenging physics associated with small dimensional systems. An example of this is capillary forces in hydrophilic systems, such as the tight retention of liquid passing through a small pore filtration membrane, or capillary force driven microfluidics where, to keep liquid flowing the dimensions of the system become so small that the flow rates are too low to be useful, or the manufacturing of such devices becomes uneconomical. This disclosure details methods to 'reset' the capillary force condition to avoid the requirement of transient pressure spikes associated with the breakthrough pressure of small pore membranes, and avoid the necessity of extremely small microfluidic channels, which can be useful in applications such as filtration of whole blood to plasma using only suction pressure or passive capillary pressure.

20 Claims, 5 Drawing Sheets

CAPILLARY PRESSURE RE-SET MECHANISM AND APPLICATIONS

CROSS-REFERENCE TO RELATED APPLICATIONS

This application is a continuation of U.S. patent application Ser. No. 16/513,518, filed on 16 Jul. 2019, which claims the benefit of U.S. National Phase application Ser. No. 15/312,311, filed on 18 Nov. 2016, which in turn claims the benefit of Patent Cooperation Treaty application number PCT/US2015/34608, filed on 7 Jun. 2015, which in turn claims the benefit of U.S. application No. 62/011,661, filed 13 Jun. 2014, all of which are incorporated herein by reference.

BACKGROUND OF THE INVENTION

Field of the Invention

The present invention relates to methods and designs for reducing the pressure required to pass liquid through a membrane for the first time, particularly in relation to use in sample processing for medical diagnostic applications. More generally, the invention discusses how a liquid exposed to or experiencing capillary forces or capillary pressure can be 'reset' from one set of governing conditions which may be characterized by requiring a high pressure to overcome, to a new set of governing conditions which may be characterized by requiring much less pressure to overcome, or to induce a continuation a flow through a system.

Description of Related Art

Many filtration systems experience a transient spike of liquid flow pressure as liquid is passing through the filtration system for the first time However, once liquid has passed through the filtration membrane, a steady state pressure is reached which can be significantly lower than the pressure spike. In large, industrial filtration systems, this transient pressure spike is usually of little concern, because the whole system is designed to withstand this spike. However, in low cost, handheld, disposable systems, managing this pressure requirement can be very difficult, expensive, or impossible.

This pressure spike is caused by the capillarity of the filtration membrane itself. If the membrane material is hydrophobic, aqueous liquid will not want to enter the membrane and the increased pressure is required to force the liquid in. If the membrane material is hydrophilic, aqueous liquid will not want to leave the membrane, but is tightly held within the pore structure of the membrane, and the pressure transient is needed to push the liquid through, or out, of the membrane (breakthrough pressure). However, once liquid is flowing through the membrane, the capillarity of the membrane ceases to exist, and flow is governed by a different set of conditions that does not include the hydrophilicity or hydrophobicity of the membrane material, but rather its pore size, percent porosity, liquid viscosity, flow rates, and any relevant downstream flow conditions. This is the steady state condition.

This disclosure will discuss hydrophilic systems, or systems where the membrane is comprised of a hydrophilic material, or where the membrane or critical surfaces of the membrane can be rendered hydrophilic.

The term Capillarity refers to capillary forces that exist at a liquid/gas interface, or liquid/air interface, where surface tension, or interface tension exists between the liquid and the air. Capillarity is dependent on the dimensions of the system, such as the pore size of the membrane, the type of liquid, e.g. aqueous or organic, salt content, etc., and the surface properties of the flow channel, such as hydrophobic or hydrophilic including the degree of hydrophobicity or hydrophilicity (contact angle). Once liquid is already pushed through a membrane, the liquid/air interface is no longer present in the membrane, which is why the capillary forces or capillarity ceases to exist within the membrane.

In contrast to pressure transients experienced by membrane filtration systems, another system, referred to as a lateral flow system, exists where no pressure transient takes place and, in fact, no externally applied pressure is required to pass liquid through a membrane. In a lateral flow system, capillary forces completely control the flow of liquid through the system. Different membranes, including filtration membranes, are layered one on top of each other, and liquid passes from one membrane to the next due to the increased capillarity of each successive membrane. A filtration membrane that is often used in such systems is the PALL Vivid™ Plasma Separation Membrane that is capable of separating plasma from whole blood. Normally such filtration, due to the small pore size, would require substantial pressure to force the plasma or serum to exit the membrane. Such high pressure often causes hemolysis, or breaking of red blood cells in the whole blood, which reduces the quality of the filtrate. Instead, according to operational instructions of the membrane itself, all that is required to extract the plasma through the membrane is to place the membrane on another membrane of higher capillarity, then flow proceeds automatically.

However, what if it is desired to remove the plasma from the membrane, or from a successive membrane? This is difficult to do using existing technologies, prior to the technology discussed in this disclosure. Instead, if it is desired to separate plasma from whole blood in a non-filtration membrane system, a centrifuge is usually used.

Many new medical diagnostic systems use microfluidic technologies to control liquid flow, process liquid samples, and analyze their content. Microfluidics involves the processing and movement of liquid through small channels, such as channels between 0.1 to 1000 µm in diameter. Liquid flow is controlled by capillary forces, positive pressure pumps, suction, or electric forces. These include the processing and analysis of whole blood. In some of these systems attempts are made to separate plasma from whole blood. However, whenever the microfluidic flow channels become very small, such as less than 1 to 5 µm in diameter, such as what may be needed to separate plasma from whole blood, the system quickly becomes impractical to commercialize due to the very expensive manufacturing methods that are required to produce products reliably with such small dimensions, or due to the extremely low flow rates that are generated, or very high pumping pressures that may be required if the system is driven by positive pressure, or because of the difficulty in sealing such a system due to high pressures or high probability of blocking small flow channels during the sealing process, or other related complication.

The use of a membrane to separate plasma from whole blood has several advantages over the use of microchannels or a network of microchannels for separation. These advantages include the fact that membranes for this purpose are already commercially available in large quantities, are relatively inexpensive, robust, durable, and easy to use. Also, their quality and manufacture can be controlled, tested and performed 'off-line' of the quality and control and manufacture of a complete diagnostic system. They do not represent a limiting factor in the production of a diagnostic device, which is in strong contrast to the use of microchannels as a means of size-exclusion based filtration.

It is highly desirable and beneficial for a system to be developed that has the advantages of membrane based filtration, but does not require the filtrate to be retained and processed within a downstream membrane system, and does not require the use of buffer, diluent, solvent, or pressure in order to cause the filtrate to be passed through the membrane and be available for collection. It is also desirable for this method of filtration, when used for medical diagnostics, to be able to interface directly with enclosed microfluidic-based diagnostics, or to be collectable and used in some macro diagnostic system, or even reintroduced to a membrane based systems after additional processing on the filtrate has taken place, such as metering or measuring the amount of filtrate that is present before it is passed downstream.

BRIEF SUMMARY OF THE INVENTION

As has been discussed, capillary forces can be used to draw plasma, or any aqueous liquid, out of a small pore hydrophilic membrane, provided these capillary forces are greater than the capillarity of the membrane itself. Once drawn out of the membrane, the capillarity associated with this membrane ceases to exist due to the removal of a liquid/air interface at or within the membrane, or at the downstream junction of the membrane and subsequent liquid flow system. The use of these capillary forces to draw liquid out of a membrane can be used to reduce or eliminate a pressure spike transient often associated with passing liquid through a small pore membrane for the first time.

This invention details for the first time a method, process and design for drawing liquid out of a small pore membrane, or out of small dimensioned microfluidic channels, by using a micro or nano-particulate salt, sugar, protein, or other material that is eventually soluble in the membrane filtrate or microchannel system liquid. Initially, due to its particulate size and pore structure, which pore structure could be generated by the spaces in between individual granules or particles, which particles or granules may or may not be porous themselves, and due to the chemical composition of the granules or particles including its hygroscopicity and ability to generate osmotic forces, this micro or nano-particulate soluble material, or soluble matrix, possesses a higher capillarity, or higher liquid drawing force than the initial membrane or microchannel to which it is in physical contact, so that the liquid passes out of its present position within the initial membrane or microchannel and into the soluble matrix component. The soluble matrix is held in a flow channel or housing or system in physical contact with the initial membrane or microchannel, but the geometry of said flow channel, housing, or system is of a much larger dimension than the pores of the initial membrane or diameter of the microchannel. Over the course of seconds to minutes this soluble matrix dissolves in the liquid that has filled its pores, and the liquid now resides outside of the initial membrane or microchannel, in a system of larger geometry where capillary forces, if they still exist, are much more manageable or lower than they were while the liquid was within the initial membrane or microchannel.

In this manner, by using a soluble matrix with high initial capillarity, liquid within the initial membrane or microchannel can be drawn out of the initial membrane or microchannel by capillary forces without the need of any additional pressure or force. Stated in another way, a soluble matrix can be used to produce a material of temporary high capillarity, useful for drawing liquid out of a membrane or microfluidic channel, which high capillarity becomes lower as the soluble matrix dissolves.

Another way to describe the use of this soluble matrix is that it acts as a capillary pressure re-set mechanism, system or valve (CPR-Valve), such that the capillary forces holding or retaining liquid at one point are overcome and re-set to the capillary forces that are defined by the geometry, material and liquid type under a new set of conditions, that are generally of a much lower capillarity than the system preceding it.

What is also useful about this design is that, by the strategic placement of the soluble matrix, and the strategic placement of a venting duct, the volume of filtrate that is in initial contact with the soluble matrix and that dissolves in it, can be excluded from the volume of filtrate that is collected or moved downstream for further processing. In this manner any negative or deleterious or interfering effect the soluble matrix may have in downstream processing of the filtrate, can be reduced or completely eliminated.

BRIEF DESCRIPTION OF THE SEVERAL VIEWS OF THE DRAWINGS

The following drawings illustrate exemplary embodiments for carrying out the invention. There are, in fact, many possible liquids that may be processed, many possible membrane or microchannel configurations, housings, flow systems, entrance and exit point designs, flow patterns, soluble matrix or CPR-Valve placements, dimensions and geometries, and liquid flow driving forces possible in various embodiments of the invention. The following examples only serve to illustrate principles discussed in this disclosure, and are not meant to be limiting in any way in converting the principles discussed in this disclosure into physical form, and are not necessarily to scale as may be used in a physical system. Like reference numerals refer to like parts in different views or embodiments of the present invention in the drawings.

DETAILED DESCRIPTION OF THE INVENTION

Figure 1:
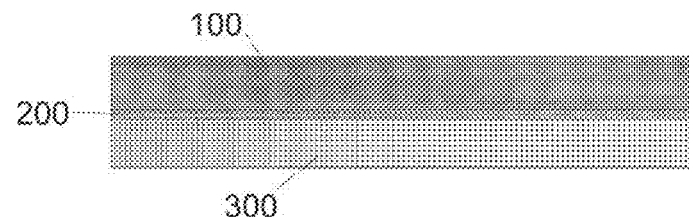
FIG. 1 illustrates a composite membrane comprised of the initial microporous filtration membrane, a macroporous bottom support membrane, and a soluble matrix held within the pores of the bottom membrane, but in contact with the bottom surface of the initial microporous membrane, according to an embodiment of the invention.

Hydrophilic membranes are often characterized by the membrane material type or composition (e.g. nitrocellulose, hydrophilic PVDF, PE, Nylon, etc.), membrane thickness (e.g. 125 µm), pore size (equivalent or average pore diameter, e.g. 0.45 µm) Bubble Point, Breakthrough Pressure (e.g. 30 psi or 207 kPa) and flow rate at a given pressure (e.g. 40 µL/min/cm$^2$ at 10 psi or 69 kPa). Other characteristics may include retention parameters of certain key materials such as red blood cells or bacteria.

Breakthrough Pressure is nearly equivalent to the Bubble Point if the same solution is used in both cases (e.g. water). The former is a factor of pushing liquid through a membrane and the latter is a factor of pushing liquid out of a membrane (using air). Both are functions of the capillary pressure equation which is dependent on pore size or equivalent pore diameter of the membrane, contact angle of the membrane with respect to the liquid used (hydrophilicity), and the surface tension of the liquid with respect to the ambient atmosphere, usually air.

Often the aqueous Breakthrough Pressure of a membrane is much higher than the desired system flow pressure. Sometimes it is even higher than the pressure a desired filter or filter holder, fittings, or other connected components can withstand. To remedy this, one could replace the desired fittings, filter holder, etc. with alternative fittings that can withstand the high-pressure that may be reached by first wetting through the membrane. Alternatively, a membrane is often wetted with solvent, which eliminates the capillary pressure by wetting through the membrane easily, after which the aqueous solution can flow more freely according to established flow parameters. Established flow parameters, or steady-state flow conditions, refers to liquid flow that is already ongoing or established in a system, rather than the liquid passing through a system for the first time. Important system characteristics that are used to define established flow include liquid flow velocity, liquid viscosity, pressure gradients, and flow channel dimensions.

Sometimes, however, it is not possible or convenient to wet the membrane with a solvent prior to use, such as if it is within an enclosed device. It may also be uneconomical, bulky, or otherwise undesirable to use high-pressure fittings. Also, depending on the application and design of the system, it may be desirable to use low pressure, such as what may be achieved by suction, to both wet through the membrane and draw the bulk liquid through the membrane such as for filtration purposes. Normally suction, when generated by electro/mechanical vacuum pumps, can only achieve a maximum suction pressure of 1 atm (14.7 psi or 101 kPa), and often much less. Mechanical suction alone, such as what may be achieved by a hand-held suction bulb, may only reach a few psi.

In some systems, such as in microfluidics, it may be inconvenient to apply any external pressure or vacuum forces at all, and require the filtration and processing system to be completely based on capillary driven flow.

Suction, however, has a number of advantages for drawing liquids into or through a system, compared to positive pressure, such as what may be achieved by a syringe or syringe pump, or capillary driven flow. Actuation of a suction bulb is typically much easier than actuation of a syringe. Mechanically, a suction bulb is typically simpler than a syringe, making it potentially easier and cheaper to manufacture. Also, with suction driven flow much larger liquid volumes may be processed than what may be practical with capillary flow.

The advantages of a syringe, on the other hand, are that a higher positive pressure can usually be generated compared to negative suction pressure of a suction bulb. Also, higher flow rates through a membrane can be generated once flow is established, due to the higher pressures that can be generated, and, potentially, some degree of volume control is possible if the volume of liquid delivered by the syringe is carefully monitored. The advantage of capillary driven flow is that the mechanics of the system can be very simple and automatic.

The purpose of this disclosure is to describe modifications to filters, filter housings or microfluidic channels that eliminate the complication of high Breakthrough Pressure, or other high pressure requirement. These modifications actually eliminate any need of an additional pressure transient beyond normal desirable flow gradients, including a case of no applied pressure gradient and just the use of capillary forces to move liquids through a filter and subsequent system. These modifications are useful because they eliminate the need of high pressure to initiate flow through a membrane. Although there are many benefits associated with eliminating high pressure requirements, this has a particular benefit of allowing suction to be more useful for flow control because it eliminates one of the disadvantages of suction flow (low pressure) and highlights its advantages (ease of use compared to a syringe and larger volumes compared to capillary pressure only systems).

Capillary pressure is often used to draw liquid through a system. Provided the drawing force of capillary pressure is greater than any backpressure that may be present, liquid can flow indefinitely. Backpressure may be generated in a capillary flow system, either at the leading or lagging end of liquid flow, if the liquid encounters a junction where the capillary pressure (as defined by the equation below) is higher in the system proximal to the junction (proximal meaning where the liquid already is) than it is at the junction, as defined by the new parameters of the new flow channel or system.

$$P = -\frac{2\sigma\cos\theta}{r}$$

where: P Capillary Pressure
r radius of pore or flow channel
θ contact angle of membrane material
σ surface tension of liquid A negative pressure is similar to a suction force that draws a liquid into the system. A contact angle greater than 90° represents a hydrophobic material, and the resulting capillary pressure turns positive, indicating a positive force is required to push liquid into the system.

If only the radius of a flow channel changes, the pressure required to force a liquid past a junction is given by the equation $$\Delta P = P(r2) - P(r1) = \frac{2\sigma\cos\theta}{r1} - \frac{2\sigma\cos\theta}{r2} = 2\sigma\cos\theta \times \frac{(r2-r1)}{r1r2}$$

where: r1=radius of flow channel proximal to the interface (where the liquid already is)
r2=radius of the new flow channel at the interface A positive ΔP indicates force, or pressure is required to push a liquid past or through the junction. If ΔP is negative, the liquid will continue to flow on its own due to the capillary pressure of the new system at the interface is greater than the capillary pressure proximal to the interface. Capillary pressure can also be termed Capillarity, so a membrane or channel with a higher capillary pressure than a first membrane or channel is said to have a higher capillarity than the first membrane or channel. When a region of high capillarity interfaces with a region of low capillarity, a capillary stop junction is formed, and force is required to push liquid past the junction or interface of the two regions.

It is important to emphasize that the capillary pressure equation is dependent on an air water (or gas/liquid) boundary where liquid is passing through a channel, membrane or system for the first time (leading end or edge of liquid flow) or where all liquid has passed through a system and is followed by air that is being reintroduced by the departure of the liquid (lagging end or edge of liquid flow), where a liquid surface tension is present. If no such boundary exits, capillary pressure is zero and flow is defined by established flow parameters, or steady-state conditions. A liquid surface tension may also exist between two dissimilar liquids, such as aqueous and organic liquids, but this is beyond the scope of this disclosure.

Liquid is drawn into a hydrophilic membrane initially by capillary forces. It is difficult to force liquid out of, or through, a membrane because at the distal (downstream) surface of the membrane, or interface, the pores open to the larger flow system, such as a tube or pipe connected to the downstream end of the filter housing, or other flow channel geometry. Referring to the capillary pressure equations above, the radius of the flow system changes from, perhaps 0.1 μm, to, perhaps 1 mm or 1 cm. In this case the pressure required to push liquid through this interface is roughly equivalent to the original capillary pressure (because 1 cm>>0.1 μm, P(1 cm)<<P(0.1 μm), so P(0.1 μm)−P(1 cm) (pressure required to force a liquid past the junction)≈P(0.1 μm).

The situation and equations discussed above describe the case when considering the leading edge of liquid flow. Capillary forces may also be present at the lagging end of fluid flow, when all the liquid has flowed through a junction and an air/liquid condition is reestablished at that junction. This renewed capillary pressure can produce a backpressure on fluid flow and possibly stop flow if it is greater than the capillary pressure experienced at the leading edge of flow. Capillary backpressure caused by the lagging end of flow can become a significant issue when considering the amount of plasma that can be extracted from a plasma separation membrane.

The reason a solvent (such as ethanol or acetone) is often used to eliminate high Breakthrough Pressure is because the surface tension (σ) of many solvents is near zero. So, the effect of a radius change in a system when the surface tension of the liquid is near zero, is relatively insignificant and the solvent can generally pass through the membrane with little or no resistance. Once a liquid is on both sides of a junction, the capillary pressure is eliminated. Normally the primary liquid of interest is added to the system soon after the solvent is added and before the solvent dries, otherwise the capillary pressure of the membrane may be reestablished. Although use of solvents to reduce the difficulty of passing an aqueous liquid through a membrane is most common with hydrophobic membranes, it may also be used when a hydrophilic membrane has a very small pore size (e.g. <0.1 μm)

An example of a system with multiple junctions where flow continues past these junctions with no applied force, is a lateral flow immuno-assay, of lateral flow test strip. In a lateral flow system multiple membranes are layered on top of each other to facilitate certain functions important to the operation of the device. For example, an initial sample pad may have a layer that absorbs and distributes a blood sample across a filter membrane that separates plasma from whole blood. The plasma is drawn through the filter by the higher capillary pressure, or higher capillarity, of another membrane below the sample pad. This second membrane may have a higher or stronger capillarity due to any one of the reasons discussed above, but usually due to a reduced pore diameter compared to the initial membrane, or a lower contact angle or higher hydrophilicity compared to the initial membrane.

While in the second membrane, the liquid (e.g. plasma) may interact with a stored reagent (e.g. conjugate) important to the function of the test. The liquid then encounters a third junction, (e.g. with a nitrocellulose membrane), where it continues to flow due to increased capillarity of this third membrane. The third (nitrocellulose) membrane often contains the test and control lines of printed biomolecules important to the function of the test. Finally, a fourth membrane is encountered, usually called the absorbing pad, that has the highest capillarity of all the membranes, providing a strong driving force to pull the liquid through the entire system.

In the example above liquid flows through multiple junctions due to increased capillarity of each new material, while within the membrane or material the liquid flows due to the capillary pressure at the leading edge of flow where a liquid/air boundary is present. Once past a junction between two membranes, the capillary forces present at that junction disappear, because the air/liquid interface has moved past the junction and a liquid/liquid condition is present at that junction. In this situation the liquid is drawn through the junction due to the capillary forces some distance ahead where the air/liquid boundary is present. The flow parameters at the junction are based on that downstream driving capillary pressure (or other drawing force, such as suction pressure generated by a suction bulb) and other established flow parameters.

Now consider a condition when the liquid has moved past the initial junction between two membranes, or two porous surfaces, due to the increased capillarity of the second porous material. As has been explained, the capillary pressure at that junction has now disappeared, and the flow conditions at that point are defined by the downstream capillarity, or other drawing force or pressure gradient. Instead of a downstream drawing force (capillary or suction pressure), the flow conditions could also be determined by an upstream positive pressure, such as what may be exerted by the displacement of a plunger in a syringe. The important factor is that, once the liquid has moved past the junction, the capillary forces at that junction have vanished.

Passing the leading edge of liquid completely through a membrane, such that it exits the membrane on the opposite side of where it was delivered, is the definition of 'Breakthrough' as used in the term Breakthrough Pressure, or how it is used in this disclosure if different than its understanding among those skilled in the art. However, in the case of the successive membranes, no pressure was actually exerted in order to push the liquid past the junction; rather it was the increased capillarity of the second material or membrane that drew the liquid through. In this manner, the high Breakthrough Pressure that may be indicated as a characteristic of the first membrane, did not actually become a factor. No excessive positive or negative pressure was exerted, only the natural capillary pressure of the second material was needed.

Now consider a situation where liquid has been drawn past a junction between an initial membrane and a second porous material, due to the increased capillarity of the second material, and then the second material is physically removed from the system. Similar to the previous case, once liquid is past the junction, the capillary forces at that junction vanish, and flow out of the first membrane continues to proceed according to established flow parameters, either due to a positive pressure on the liquid upstream of the junction, or a negative pressure downstream of the junction, such as what may be exerted by a suction bulb, or due to a secondary capillary driving system such as small flow channels placed next to the second porous material that has since been removed.

Instead of removing the second porous material that has drawn the liquid past the junction, consider further a case where the second material dissolves in the liquid that has filled it's porous structure. Similar to the case described above, because the liquid has already past the junction, capillary pressure at that junction has already disappeared, no high Breakthrough Pressure was required, and flow may continue under established flow parameters either due to an upstream positive pressure or downstream negative pressure or another capillary driving system.

In this manner, by using a porous material that is comprised, at least in part, of a component that is soluble in a liquid passing through it, and placing it in physical contact with the downstream surface of an initial membrane, which porous material, before the soluble component dissolves, possesses a higher capillarity than that of the initial membrane, and which porous material after the soluble component dissolves, if any remains, represents no significant barrier to established flow, then the initial membrane's Breakthrough Pressure is effectively eliminated.

Although the nature of the liquid may have changed slightly by having a component of the second porous material become dissolved in it, thus change can be tailored to be only a small change in surface tension (either increased or decreased) and/or only a slight change in viscosity (either increased or decreased), which are the liquid parameters important in governing established flow.

This new system can be described as a Composite Membrane comprised of multiple parts. A three component composite membrane is illustrated in FIG. 1. It consists of: an initial membrane 100 which controls the filtration parameters; a porous soluble component or soluble matrix 200; and another material 300 with larger pore structure than the initial membrane which serves to support or hold in place the soluble matrix 200 and put it in direct physical contact with the initial membrane 100. Depending on the design of the system, the third component may not be needed, but if used it also controls the actual Breakthrough Pressure of the entire system.

The effective capillarity of the soluble porous material, or soluble matrix, must be higher than the capillarity of the initial membrane. This higher capillarity, or ability to draw liquid past the capillary stop junction can be based on the relevant parameters shown in the capillary force equation, but also due to the chemical nature of the soluble matrix including ability to generate osmotic forces and or its hygroscopicity. The liquid must enter the pores of the soluble matrix before it dissolves, so that the liquid is on both sides of the junction between the initial membrane and soluble matrix. This will eliminate the capillary pressures at the junction and eliminate the Breakthrough Pressure of the initial membrane. If this condition is not satisfied, such as if the soluble matrix dissolves in the liquid while the liquid is still within the initial membrane and has not yet moved past the junction or exited the initial membrane, which may take place if the soluble matrix is not porous, then the high Breakthrough Pressure of the initial membrane still exists.

Provided no significant capillary pressure is present at the lagging end of liquid flow, the ongoing flow is determined by the new system where the soluble matrix has been placed. However, the capillarity of the initial membrane can still be important if the lagging end of liquid flow, where a liquid air interface exists, begins to enter the upper surface of the initial membrane (e.g. all liquid placed on the initial membrane has now entered the membrane and is no longer pooled on the upper surface of the membrane). In this case, the overall movement of filtrate is determined by a balance of the capillarity on the leading end of flow and backpressure that may be generated on the lagging end of flow.

In this case flow through the membrane may stop. However, in some designs, as discussed later in this disclosure, a venting duct may be present downstream of the initial membrane so that filtrate that has already passed through the membrane and into the area downstream of the membrane, may still be collected or moved forward either by suction, capillary pressure, or positive pressure—placed at the point of the venting duct rather than upstream of the membrane which can cause membrane damage or cell lysis if whole blood is being filtered.

For the soluble matrix and this design to function properly, it is required that the initial membrane and the downstream flow system where the soluble matrix is placed, are hydrophilic or can be rendered hydrophilic by some secondary process such as UV or plasma treatment or film coating.

Micro/Nano Particle Soluble Component. The porous soluble component may be a simple salt, such as sodium chloride (NaCl), or it may be a more complex organic salt, such as a low-viscosity cellulose salt or an anhydrous acid or base, such as ethylenediaminetetraacetic acid (EDTA), or it may be a sugar such as sucrose or dextrose, or sugar derivative such as Heparin. It may also be a soluble protein or other material. Some salts, sugars, proteins or anhydrous acids or bases (collectively referred to as the soluble matrix) may be inappropriate for the filtrate being collected, or it may impart undesirable features or components to the filtrate. However, some soluble components may be favorable, such as those that help preserve beneficial features of the filtrate, or do not interfere with downstream analysis or processing of the filtrate.

In the case where the soluble matrix adds desirable features to the filtrate, the soluble matrix can be collected together with the filtrate for downstream processing. In the case where the soluble matrix interferes with downstream filtrate processing or analysis, it can be excluded from the volume of filtrate moved downstream or collected. How this portion of the filtrate can be excluded is discussed later in this disclosure.

It is also desirable that the soluble matrix, due to its placement in physical contact with the initial membrane where it may be stored for a significant amount of time, is not reactive or damaging to the membrane.

To form a micro- or nano-porous structure the soluble matrix may need to be ground to a very fine powder. The porosity of the soluble matrix may be a factor of the spaces between the soluble material, rather than any actual porosity in the material itself. The important parameter of the soluble matrix is its capillarity compared to that of the initial membrane, which may be a component of its grain size, but also of its material chemistry including being hygroscopic or being able to generate osmotic forces to draw liquid past a capillary stop junction. The rate of dissolution of the soluble matrix in the filtrate of the initial membrane is also critical, and is also a factor of chemistry and grain size. These will need to be optimized according to the needs of the system.

The soluble matrix may be comprised of both soluble and insoluble materials where the insoluble material is held together by the soluble material. In this case the combined material may disintegrate when exposed to the filtrate rather than actually have a significant amount of the material dissolve in the filtrate. An example of this may be an insoluble neutral and non-reactive polymer powder bound together by soluble sugar linkages. Once wetted by the filtrate, the matrix may disintegrate which can serve basically the same function as dissolving, provided the disintegrated material does not represent a barrier to or interfere with downstream flow or processing of the filtrate.

The soluble matrix can be generated by mixing the components of the matrix in a solvent that only weakly dissolves the material, or weakly dissolves only the soluble component of the material. For example, if the matrix is to be comprised of a simple sugar, then a solvent, such as anhydrous acetone or ethanol that does not significantly dissolve the sugar, is combined with 1 or 2% water, which does dissolve the sugar. The resulting mixture or solvent and powder can be described as a slurry. A very small portion of the sugar slurry does dissolve in the solvent, but most of it remains undissolved. When the solvent evaporates the remaining material is a semi-pliable porous material that can be placed in the appropriate position in physical contact with the initial membrane. In another example the matrix may be comprised of an insoluble powder and a small amount of soluble sugar, to which water is added. The sugar dissolves in the water, but the insoluble powder does not dissolve and the mixture again forms a slurry. When the water evaporates the insoluble powder is bound together by the sugar that has dried on its surface and formed connections or bridges between the powder particulates. Again, this matrix can be placed in its desired position in physical contact with the bottom surface of the initial membrane and the upper surface of the base material.

Before the solvent evaporates from the slurry, the slurry can be pressed into a film of desirable thickness. It may also be possible to spin dry the slurry or matrix into a thin film, which may be useful for some designs, as thin films of resist are spun onto semiconductor substrates. It may also be possible to spin-dry the soluble matrix into a fibrous material that can be collected as a type of fibrous membrane that is pressed to the appropriate thickness and cut to size.

It is also favorable that the material used for the soluble matrix not swell significantly in the presence of the filtrate, due to potential damage to the initial membrane that may result and due to the fact that it may absorb the filtrate rather than dissolve in it. Although being hygroscopic may add some desirable feature to the soluble matrix, it should not be too hygroscopic, both because of the difficulty in preserving and storing hygroscopic materials and due to the fact that many hygroscopic materials can absorb a significant amount of liquid before dissolving in it.

Figure 2:
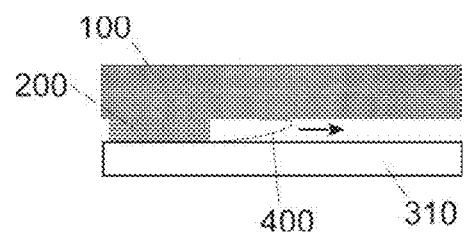
FIG. 2 illustrates a simplified version of composite membrane design where only a small portion of the soluble matrix is used and the system is comprised of the initial filtration membrane and the soluble matrix held in contact with a portion of the bottom surface of the filtration membrane. This soluble matrix is within a housing holding the filtration membrane, holding the soluble matrix in contact with the membrane, and providing a flow channel for the filtrate once it passes through the filtration membrane, according to an embodiment of the invention.

Minimizing the Amount of Soluble Matrix Required. The mechanism of action to eliminate the breakthrough pressure of the initial membrane is to use the higher capillarity of the soluble matrix to cause the filtrate to break through the downstream or bottom surface of the initial membrane, and then have the capillary pressure inherent to the soluble matrix disappear by the soluble matrix dissolving in the filtrate. As has been explained the breakthrough pressure caused by the capillary pressure of the initial membrane disappears because filtrate is now on both sides of the junction between the bottom surface of the initial membrane and whatever is immediately adjacent to it. However, consider a condition when filtrate has broken through the downstream surface of the initial membrane in only one location. As this filtrate passes through the initial membrane at this location it may spread-out and travel along the downstream surface of the initial membrane. This is illustrated in FIG. 2. The driving force of this spreading is the hydrophilic nature of the downstream or bottom surface of the initial membrane 100 and the hydrophilicity of the base material 310, and the formation of a meniscus between these surfaces 400. This spreading is not caused, or is not caused very much by, the continuation of flow of filtrate through the initial membrane at the one location where the soluble matrix 200 was present, but because the whole bottom surface of the initial membrane 100 is saturated with filtrate that is waiting to penetrate the last few micrometers of the bottom porous structure of the initial membrane. The spreading meniscus 400 formed between the bottom surface of the initial membrane 100 and the upper surface of the base material 310 is enough to bridge this final gap in flow of the filtrate waiting to break through the bottom surface of the initial membrane 100. This is done by wetting through this final gap from the side of the membrane where the meniscus is present. The meniscus 400 moves or flows tangentially across the whole bottom surface of the initial membrane 100 not because of continued flow through the initial breakthrough point, but because of flow normal to the surface of the initial membrane 100 that simply adds to the volume of filtrate that has passed through the membrane and causes the meniscus 400 to spread.

This spread initiates at the point of the soluble matrix 200 and moves outward or away from this point depending on the structure of the open area between the bottom surface of the initial membrane 100 and the base material 310. In this manner, the total surface area of filtration can be increased without necessarily increasing the amount of soluble matrix 200 required for the system to function.

Plasma Separation from Whole Blood. Referring again to FIG. 2, an example of one embodiment of the Composite Membrane System is a plasma separation system that uses the Pall Vivid Plasma Separation Membrane (PSM) 100 with a minimum, or bottom, pore diameter of between 0.05 to 0.8 μm. The soluble matrix 200 may be a finely ground EDTA powder placed between the bottom surface of the PSM 100 and the top surface of the base material 310, which may be polyethylene terephthalate, or PET. The thickness of the soluble matrix 200 between the surfaces may be between 25 to 250 μm, defined by an adhesive layer connecting the PSM 100 to the base material 310 (not shown in FIG. 2 but illustrated in later figures). The porosity, or approximate pore size, of the soluble matrix 200 may be between 0.01 to 0.04 μm, compared to the pore diameter of the PSM 100. This, together with the material composition represents a region of higher capillarity than the PSM, thus plasma passes into the soluble matrix 200 and out of the PSM 100.

It is important that the plasma passes all the way through the soluble matrix 200 such that is contacts the bottom surface of the new flow system (the base material 310), before the soluble matrix dissolves. If it does not reach both surfaces, or remain in contact with both surfaces, a meniscus 400 bound by both surfaces will not be formed. This meniscus 400 is required for the downstream capillarity of the system to be able to cause the plasma to continue to flow.

Once the soluble matrix 200 dissolves, the capillarity of the new flow geometry takes over and governs continued flow, until the time when capillary pressure of enough significance is generated at the lagging end of liquid flow, which would be the liquid remaining in the PSM 100, which could stop further flow as has been discussed.

The amount of plasma collected from a PSM is directly proportional to the amount of blood added and surface area of PSM used. As has just been described, an increase in the surface area of the PSM may not necessarily require an increase in the amount of soluble matrix required. The composite structure can be designed such that the total surface area of contact between the PSM and the soluble matrix, where the soluble matrix is located, is kept low, as is illustrated in FIG. 2.

Figure 3:
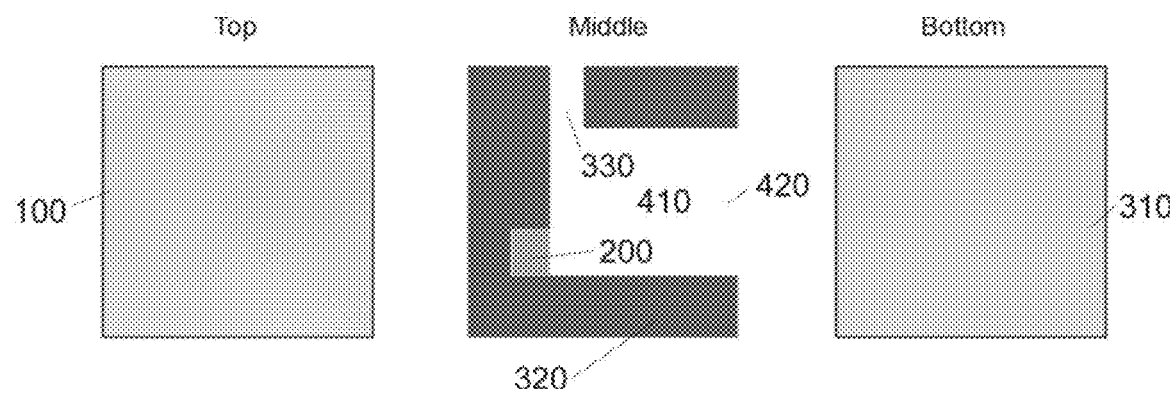
FIG. 3 illustrates a design where, by the strategic placement of a venting duct, the soluble matrix that initiates flow of filtrate through a membrane can be excluded from the volume of filtrate that is extracted or collected from a filtration device, according to an embodiment of the invention.

Exclusion of the Soluble Matrix from the Collected Filtrate. FIG. 3 can be considered a layer by layer view of the illustration of FIG. 2, but it also shows an additional feature not illustrated in FIG. 2, namely the presence and placement of a venting duct 330. If filtrate breaks through an initial membrane 100 by passing into the soluble matrix 200 due to the soluble matrix high capillarity, it may generate the meniscus between the initial membrane 100 and the base material 310, as has been discussed. This meniscus may spread through the entire open area under the initial membrane 410. However, although the meniscus has spread, there may be no or very little movement of the filtrate that actually passed through the initial membrane 100 and dissolved the soluble matrix 200. As was explained, the meniscus spread is due to the expansion of the surface area of the initial membrane 100 where filtrate was passing through.

Except by the process of diffusion, the initial filtrate that passed through at the point of the soluble matrix, has not moved, nor has the soluble matrix 200 moved, other than dissolving in the filtrate and very small movement driven by diffusion and very little continued flow at this one point on the membrane. The filtrate at this point has a high concentration of soluble matrix, and the filtrate at all other areas under the initial membrane 100 has very little or no soluble matrix in it.

Consider a case where it is desired to extract the filtrate that has passed through the initial membrane 100, either by downstream capillary forces or suction or other driving force. Due to the balance of capillary forces downstream of the membrane and within the membrane caused by the presence of the air/liquid interface of the lagging end of liquid flow, it would be very difficult to extract any more filtrate out of the membrane 100 to allow continued flow of the filtrate that has already passed through the membrane 100 to be moved further downstream, without the presence of a venting duct 330. In the case of a plasma separation membrane, the pores of the membrane would also be clogged with cells, making further flow through the membrane difficult. With the presence of the venting duct 330, the filtrate can move forward, evacuating the area underneath the membrane 100, with the space that was previously filled with filtrate 410 now replaced with air (or something else) that has entered through the venting duct 330.

However, by the strategic placement of the soluble matrix 200, and the strategic placement of the venting duct 330, as shown in FIG. 3, the volume of filtrate that has a high concentration of the soluble matrix 200, can be excluded from the volume of filtrate that is moved downstream, either by suction or capillary force at the point of filtrate extraction 420, or positive pressure exerted at the point of the venting duct 330.

Figure 4:
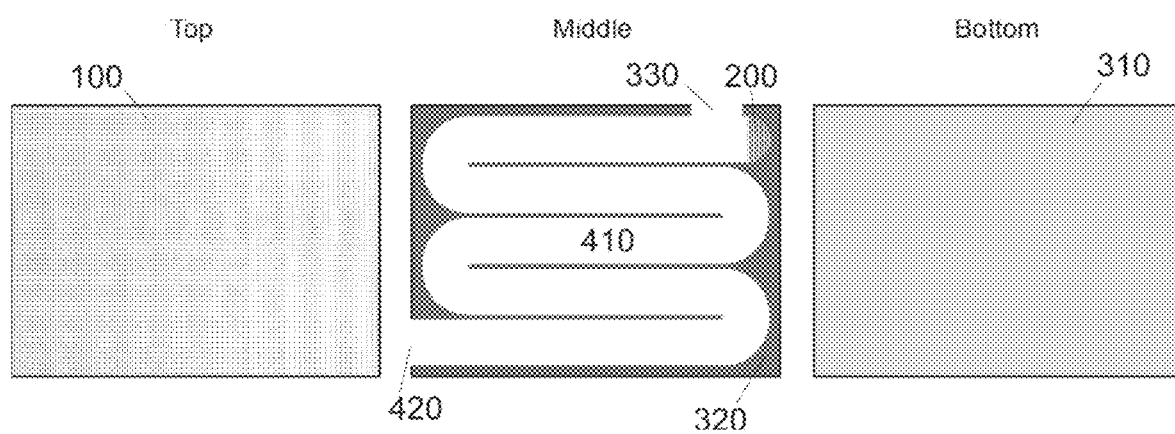
FIG. 4 illustrates a large surface area membrane used for collecting a large volume of filtrate from a large input sample, and the implementation of a venting duct and serpentine channel for collecting the filtrate, according to an embodiment of the invention.

This is further illustrated in FIG. 4, which involves a serpentine channel 320 formed in an adhesive layer that covers a large portion of the bottom surface area of the initial membrane 100. The serpentine channel 320 may be helpful for ensuring no bubbles are trapped underneath a large surface area system, when the filtrate is collected or moved downstream of the initial membrane 100. As is illustrated, the area of the soluble matrix 200 does not contribute to the volume of filtrate 410 between the venting duct 330 and the filtrate collection point 420, but is effectively bypassed. This area would be included if the venting duct 330, as shown in FIG. 4, were immediately to the right of the soluble matrix 200, but it is not. It is to the left and above the point of the soluble matrix 200, thus the volume of filtrate that has passed through the initial membrane 100 at that point remains under the membrane and is not moved downstream of the membrane.

It is important that, when liquid is added to the upper surface of the initial membrane 100 that it covers and saturates the entire surface of the membrane. The capillarity of the membrane is significant, and still plays a role in liquid movement once filtrate has passed through the membrane, even if it has spread significantly underneath the membrane. It is entirely possible, and has been observed, that if the membrane is not completely covered and saturated, that filtrate that has passed through the membrane at one point can be drawn back into the membrane at another point where the high capillarity of the membrane may still exist, due to the fact that the membrane at that other point has not been saturated. In the example of plasma separation from whole blood discussed previously, the capillarity of the bottom surface of the PSM is governed by flow channels within the range of 0.05 to 0.8 µm in diameter, whereas the effective diameter of the flow channel under the PSM is closer to 25 to 250 µm. In this case plasma will be drawn back into the PSM if its upper surface is not covered and saturated with whole blood.

Blood may be aided in its distribution across the top surface of a PSM by a close fitting cover comprised of a hydrophilic material that aids in channeling the blood by capillary action across the whole PSM surface rather than pooling at only one location where the blood may be introduced. This is illustrated in later figures.

There are many possible configurations and geometries of the initial membrane, microchannel, and soluble matrix, many possible soluble matrix materials can be used, and many possible applications can be developed. Whether it is serum or plasma that is produced, or other subcomponent of whole blood, or subcomponent of any other liquid sample added to the initial membrane, depends on the specifications of the membrane used. Applications are discussed below and include microplate filtration, large volume filtration of whole blood to plasma, an integrated small volume plasma separation from whole blood device using capillary driven flow, a 'stand-alone' whole blood hematocrit measurement device, a method of removing plasma for the collection of blood cellular components, a tool for automatic input sample volume metering, and a method of overcoming the capillary stop junctions of one or multiple small microfluidic channels.

Microplate Filtration. There are many microplates that include filtration membranes at the base of each well. Usually these microplates are spun in a centrifuge or placed in a fixture connected to a vacuum pump in order to drive liquid through the filter. High pressures are required to both initiate flow through the filters, due to the breakthrough pressure of the filters, and to generate appropriate pressure gradients to drive liquid through the filters under established flow conditions. Using the designs shown in FIGS. 1 and 2, the high pressure requirement to initiate flow is eliminated. Depending on the application, the need to use any form of added pressure could also be eliminated or significantly reduced. Microplate filtration is often used to wash beads or bound biomolecules held within the wells of the microplate. This structure would reduce the suction force or centrifugal spinning speed that may otherwise be required for the filtration process to take place.

Whole Blood Filtration Cartridge. In the design for large volume whole blood filtration, the total blood volume may be around 300 to 1000 µL, with the collected plasma volume around 50 to 300 µL. In this case the plasma filtrate could be collected in a specimen chamber to be used later for multiple diagnostics, or it could be re-deposited directly into a diagnostic system, or mixed with other reagents and stored or immediately used. The value of suction over capillary driven flow is that it can facilitate larger flow rates for faster collection and can overcome small capillary stop junction pressures for collection into a large diameter collection vessel (large compared to the dimensions of the flow channel underneath the plasma separation membrane).

Figure 5:
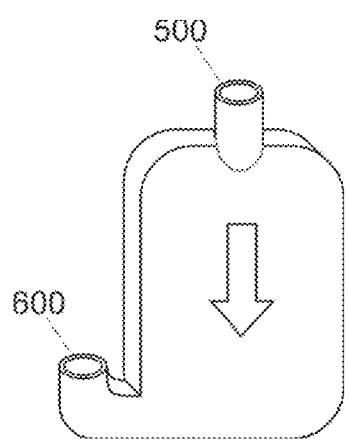
FIG. 5 illustrates a cartridge for extracting a filtrate, such as plasma, from a complex liquid sample, such as whole blood, with a sample inlet port and a filtrate or plasma collection fitting. The arrow shows the direction of filtrate flow. The filtrate collection device may use suction to aid in collecting the filtrate from the cartridge according to an embodiment of the invention.

This design is illustrated in FIG. 4 and FIG. 5. A large surface area PSM 100 is used, such as around 10 cm² of the Pall Vivid GR PSM. As shown in FIG. 4, an adhesive spacer 320, between 25 to 250 um thick, is used to form a serpentine channel winding back and forth underneath the PSM 100. This is done to ensure no bubbles are trapped underneath the PSM while the meniscus moves forward from the point of the soluble matrix 200 to the point of plasma collection 420. The serpentine channel is also used to ensure no liquid is trapped as the plasma is extracted from the point of the venting duct 330 to the point of plasma collection 420. The actual width of the serpentine channel is optimized empirically, but is probably around 1-4 mm. The thickness of the walls of the serpentine channel adhesive 320 are minimized so that they can still support the PSM 100, but also allow the maximum possible surface area of the PSM to be exposed to the area of plasma collection 410. The venting duct 330 is placed in a strategic location to maximize the collection of plasma, but also to prevent the plasma with a high concentration of soluble matrix 200 from being collected, if it is not desired.

FIG. 5 illustrates the macroscopic view of the separation device formed in the shape of a cartridge with fittings for whole blood introduction 500 and plasma extraction 600. When a whole blood sample is connected to the cartridge input 500, the blood enters the cartridge by gravity, positive pressure, suction or capillary force. Once within the cartridge blood spreads across the whole surface area of the PSM by capillary force. Once plasma has spread through the serpentine channel underneath the PSM, by the mechanism that has been explained, it can be collected into a vessel connected to the cartridge output 600.

The collection point of the cartridge output 600 is connected via a flow channel to the plasma collection point at the end of the serpentine channel 420 shown in FIG. 4. The plasma can be pushed into the collection vessel by positive pressure applied at the point of the venting duct 330, or it can be drawn into the collection vessel by suction pressure applied by the collection vessel itself, or something connected to the collection vessel.

Provided any applied air pressures are kept low, air will not pass through the PSM when suction or positive pressure is applied to the serpentine channel because the dimensions of the serpentine channel, with an effective diameter of between 25 to 250 µm compared to the pore diameter of the PSM being within the range of 0.05 to 0.8 µm, causes flow to be much easier to pass through the channel rather than through the PSM. If the pressure generated to push or suck liquid through the serpentine channel is only in the few psi range, air will never be pushed through the PSM.

Integrated Plasma Separation from Whole Blood. FIGS. 2 and 3 illustrate the design of a small volume plasma separation device capable of integration into a microfluidic-based or membrane-based diagnostic system. The design of an integrated plasma separation system consists of a multi-layered system where the plasma separation membrane (PSM) 100 is cut to the appropriate size and is held underneath by an adhesive layer 320. The adhesive layer 320 can be between 25 and 250 µm thick. If larger than 250 µm it may be difficult for the meniscus 400 to properly form that bridges the gap between the PSM 100 and the base material 310. This meniscus 400 is critical for the separation to proceed.

After blood is placed on the upper surface of the PSM 100, it spreads across the whole PSM by wicking or capillary action, possibly assisted by a close fitting hydrophilic cover illustrated in later figures. The PSM 100 becomes saturated with the blood sample which is drawn through its pores by internal capillary forces. The high capillarity of the soluble matrix 200 underneath the PSM 100 draws the plasma through the PSM at the point of contact. The plasma fills the pores of the soluble matrix and touches the base material 310. The soluble matrix 200 can be held in place under the PSM by placing it between the PSM 100 and the base material 310 and/or by placing it in contact with the adhesive 320 that forms the walls of the space under the PSM 100.

As the soluble matrix dissolves or disintegrates by dissolution of a part or all of the soluble matrix by the plasma that has filled its pores, a liquid bridge or meniscus 400 is formed between the PSM 100 and the base material 310. As more plasma passes through the PSM at the point of the liquid bridge or meniscus 400, the meniscus expands, breaking the capillary barrier along the bottom of the PSM 100 as it moves. Eventually, the entire open area under the PSM 410 is filled with plasma that has passed through the PSM.

At the plasma collection point 420 as shown in FIGS. 2, 3 and 4 another microchannel may be present (not shown) that is smaller in effective diameter than the space under the PSM. Alternatively, another membrane may be present instead of a microchannel, which membrane possesses higher capillarity than the space 410 under the PSM 100. Plasma may continue to flow into this microchannel or membrane as the volume of plasma passing through the PSM 100 expands. If the movement of filtrate has stopped, due to the action of backpressure capillary forces caused by the lagging end of blood flow entering the smaller pores of the PSM, the plasma may continue flowing into the new microchannel or membrane due to presence of the venting duct 330 which allows the plasma under the PSM to be vacated by allowing air, or another material, to replace it. As has been discussed, the strategic placement of this venting duct 330, together with the strategic placement of the soluble matrix 200 which initiated the breakthrough process, can allow the volume of plasma with a high concentration of the soluble matrix, to be excluded from the volume of plasma that is moved downstream of the PSM. Thus an effective integrated plasma separation system is achieved with potential interface to a microchannel or new membrane based system.

Figure 6:
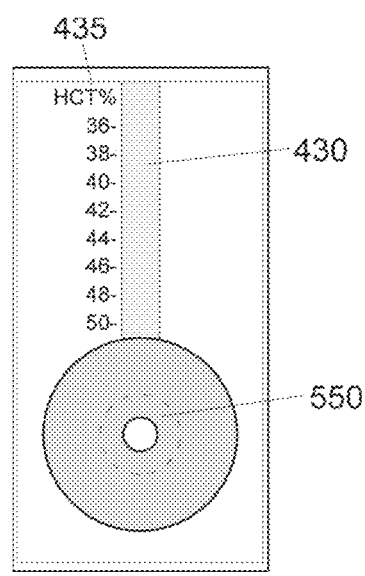
FIG. 6 illustrates a disposable hematocrit measurement device made possible by the plasma separation technology discussed in this disclosure, according to an embodiment of the invention.
Figure 7:
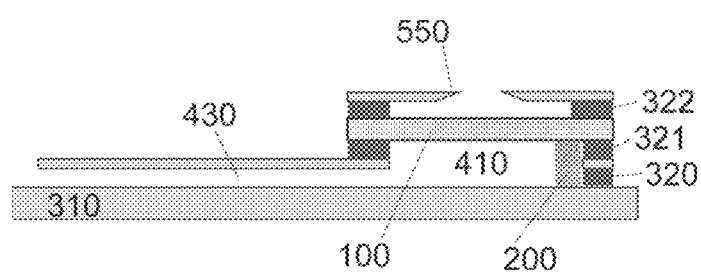
FIG. 7 illustrates a side view of the layers comprising a disposable hematocrit measurement device, according to an embodiment of the invention.
Figure 8:
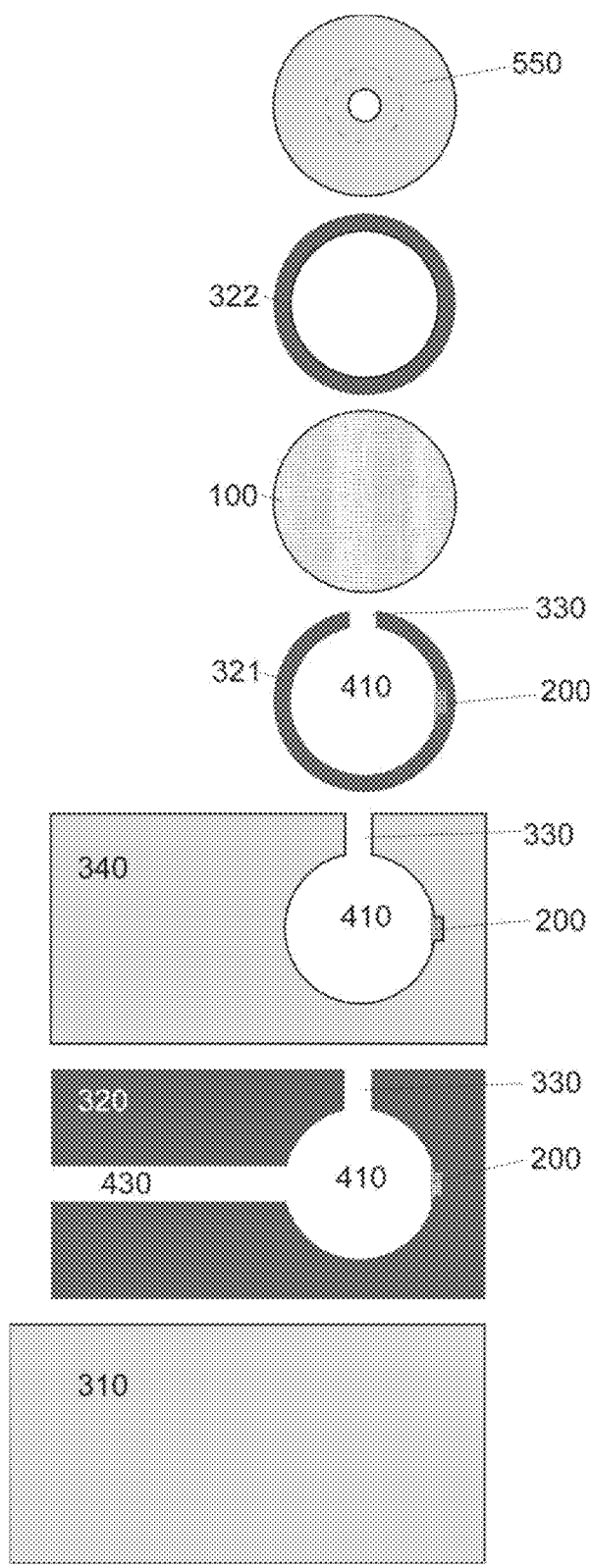
FIG. 8 illustrates a layer by layer detail of the components of a disposable hematocrit measurement device, according to an embodiment of the invention.

Stand-Alone Hematocrit Test Kit. FIGS. 6, 7 and 8 and illustrate the components and design of an integrated, analog, disposable hematocrit test kit (HTC). The function and operation of the HTC is exactly as has been described in the integrated plasma separation kit discussed above, although in the figures a lid 550 and lid spacer 322 are shown, which are not included in the previous figures. Also shown is the microchannel 430 placed at the plasma collection point 420 under the PSM 100. Rather than connecting to a downstream processing or detection system, as would be the case in an integrated microfluidic diagnostic system, the function of the microchannel 430 in this case is to allow the plasma that has been generated to be measured, this measurement is directly proportional to the hematocrit level in the blood sample used. This is true if, in all cases, the volume of blood applied to the PSM is exact and remains constant from test to test, and the surface area of the PSM remains constant and is exact from test to test. This also assumes that the separation and other characteristics of the PSM remain constant from test to test, which can be quality controlled and guaranteed by the PSM manufacturer and again by the kit manufacturer.

When the surface area and specifications of the PSM remain constant, and the volume of blood delivered to the HTC kit is repeatable, then the volume of plasma produced by the HTC kit is directly proportional to its hematocrit level. This can be measured by how far the plasma moves up the microchannel 430, as measured by the measurement column 435 as shown in FIG. 6.

If a venting duct 330 is used, as is shown in the layer by layer illustration in FIG. 8, then the plasma produced that has filled the pooling area 410, will move into the column 430 and the design has changed to a plasma separation and metering concept with an interface to a microchannel 430 for downstream processing rather than a hematocrit measurement test kit because the amount of plasma generated is only enough to fill the pooling area 410, rather than maximizing the amount of plasma drawn through the PSM which would be the case if no vent 330 is present. If the thickness of the adhesive layers 320, 321 and 322 is kept very small and no venting duct is present, some plasma will remain under the PSM 100 but also a significant portion will pass into the channel area 430 for hematocrit measurement.

As plasma is mostly clear, rather than opaque red like whole blood, it may be difficult to see visibly in the hematocrit measurement column 435, which is likely made of clear plastic layers. In this case it may be helpful if some contrasting agent or method is used, such as a dye or paper that changes color when wetted, a matte or translucent surface finish that turns clear when wetted, or something similar. It is also helpful if the leading edge of plasma flow within the measurement channel 430 is marked, such as by a color change, in the case that the leading edge retreats slightly back down the column due to evaporation, leakage, or other process. Also, in comparing FIGS. 7 and 8, it can be seen that the venting duct 330, if used, soluble matrix 200, and plasma pooling area 410, span multiple layers and are not meant to be individual components within these layers.

Collection of Blood Cellular Components, Cell Sorting or Flow Cytometry Application. One of the reasons for separating whole blood into its components is so that these components may be studied separately. While this disclosure focuses on the use of plasma extracted from whole blood, once that plasma has been extracted, the cellular components could also be studied. If an asymmetric PSM is used, the platelets will be trapped deep within the body of the membrane. The red cells may also be difficult to retrieve; however, the larger white cells should mostly be accumulated either on the surface, or only shallowly buried within the membrane, and could be removed by scraping the surface of the PSM to collect the material on top.

Instead of using an asymmetric PSM, it is possible that multiple, thin membranes could be used, with successively smaller pore sizes, which pore sizes are designed for trapping the majority of a specific cell type within the same size range. This way each membrane containing cells of a particular size range can be removed and extracted, such as by back-flow of liquid through the membrane, and studied separately.

Referring to FIG. 1, usually liquid can move from larger to smaller pore sized membranes, especially if the membranes are of the same material, by passive capillary forces. Smaller pore sized membranes usually translates into higher capillarity drawing liquid into them, if they are hydrophilic. However, if a large sample volume is used, or a sample is followed by a wash solution, there may be too much liquid for a few layers of membranes to absorb. In this case, and is illustrated as membrane 300 in FIG. 1, it may be useful for an inexpensive and relatively large pore sized depth filter to be used to absorb all excess liquid. The interface between a small pore sized membrane, such as 100, and the depth filter 300, would be the soluble matrix 200, to facilitate movement of the liquid into the depth filter. An example of a depth filter is a thick glass fiber woven membrane around 600 to 1200 μm thick with nominal pore size between 1 to 3 μm made by Pall Corporation, SKC Inc., Millipore and others.

Allowing excess liquid to drain through multiple membranes and into a depth filter by passive capillary action can allow for easier retrieval or elution of viable cells within or on top of the membranes, rather than if the excess solution is forced through such as by positive pressure applied with a syringe.

Figure 9:
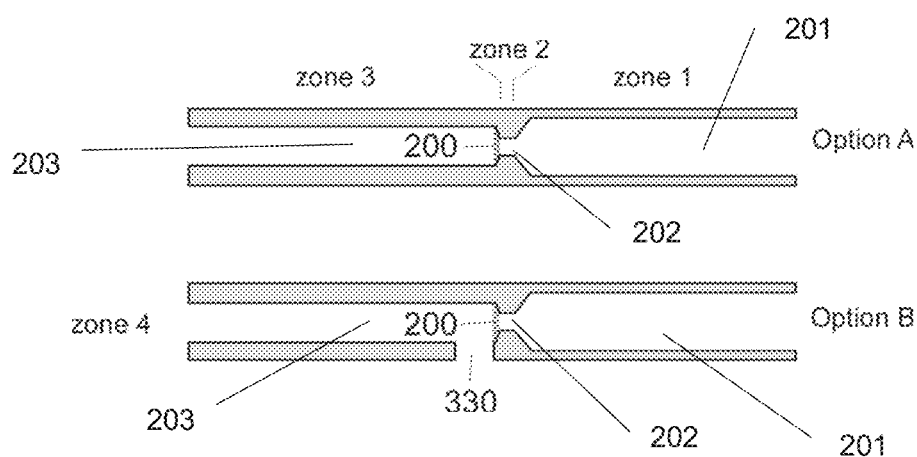
FIG. 9 illustrates two versions or options for the design of an automatic input sample volume metering device made possible by the technology discussed in this disclosure, according to an embodiment of the invention.

Automatic Input Sample Volume Metering. In the standalone HTC measurement application it was discussed that the volume of blood delivered to the PSM must remain constant and repeatable from test to test. This volume can be controlled and exactly metered by use of a precision pipetting system, such as by pipetting an exact volume of whole blood from a blood specimen container and placing in the kit. This volume can also controlled by using an exact, automatic, input sample volume metering tool made possible by another implementation of the same soluble matrix or CPR Valve that has been discussed. This device is illustrated in FIG. 9.

Capillary forces are automatic. An exact volume of sample, of blood or any other aqueous liquid, can be collected by touching a precisely dimensioned (cut to length) capillary tube to the sample to be measured. Assuming enough sample exists to fill the tube, the tube will fill automatically by the liquid passing through the inside channel until it reaches the open end of the tube on the opposite side of where the sample is introduced. The open end of the tube represents a capillary stop junction. It does not actually need to be completely open, but it needs to be larger in effective diameter than the capillary tube itself.

Instead of a single capillary of one uniform diameter, consider a capillary with an initial diameter A1 201, leading to another very short section of the tube with a smaller diameter A2 202, which then leads to another section, with diameter between A1 201 and A2 202, called A3 203. This is illustrated as Option A in FIG. 9 and labeled as zone 1 (for the section with diameter A1), zone 2 (with diameter A2) and zone 3, with diameter A3 where A2<A3<A1, 201 202 203, respectively.

The flow of liquid, such as blood, when the capillary tube is placed in contact with the liquid at the open end of zone 1, will be to automatically fill zone 1 and zone 2, and stop at the intersection between zone 2 and zone 3, where the smaller diameter A2 202 opens up to the larger diameter A3. This enlargement of the channel diameter represents a capillary stop junction, as has been explained. Once flow has stopped at this point, the capillary tube is removed from the liquid source. The filling process should only take 1-3 seconds, after which the liquid source is removed.

A CPR-Valve 200 in the form of a thin section of soluble matrix is placed at the junction between zone 2 and zone 3, the liquid that has stopped at this point will fill the pores of the soluble matrix and move past the junction, filling the initial section of zone 3. At this time the stopping force of the capillary stop junction is overcome by the increased capillarity of the soluble matrix. Since liquid (blood) is now on both sides of the stop junction, the capillary forces that held the liquid at that point vanish. Because the capillarity of zone 3 is higher than the capillarity of zone 1 (smaller diameter), the liquid volume in zone 1 will pass into zone 3 by capillary action. The liquid will fill zone 3 until, either, it reaches the end of zone 3 where another stop junction is present, or the lagging end of flow reaches the junction of zone 2 and zone 1, where a strong capillary pressure is re-introduced.

In this example, the volume encompassing zone 1 is the metered volume of sample which has been automatically metered and delivered into zone 3, assuming zone 3 is large enough to accept the entire zone 1 volume. The volume of zone 2 represents a dead volume which is held within the inlet port and not passed on.

In most applications zone 3 is actually not a part of the capillary tube inlet, but is actually the first section of the downstream device, such as the plasma separation membrane 100 of the HTC test kit. Referring to FIG. 7, the inlet hole and cover 550, together with the adhesive spacer 322 and upper surface of the PSM 100, can be designed to have a higher capillarity than zone 1 of the metering tool.

It is possible that this HTC input section, or any input component of an integrated device, could have a higher capillarity than zone 2 of the metering tool. If this is true then the metered volume is a combination of the volume of zone 1 and 2. But, it must have a higher capillarity than at least zone 1, otherwise the device will not function.

In the case where the high capillarity of zone 2 represents a barrier to ongoing flow of liquid through the system, such as into zone 4 of Option B, then Option B may be a better design where the high capillarity of zone 2 can be bypassed by the presence of a venting duct 330 at the inlet side of zone 3. In this design the high capillarity of zone 2 does not prevent flow of liquid further downstream of the metering tool. However, the capillarity of zone 3 could still be a limiting factor, depending on the overall design of the downstream portion of the kit.

This metering tool is useful for any aqueous liquid. However, due to the fact that blood is a very viscous and complex liquid, it is important to design the CPR-Valve 200 such that it does not stop the flow of blood altogether. The porosity of the CPR-Valve can be quite large in this case, compared to the porosity of the soluble component in the plasma separation design. For example, if the diameter of zone 2 is around 100 µm, then the average pore diameter of the CPR-Valve could be up to 50 µm, compared to 0.050 µm as it may need to be in the plasma separation application.

Also, whereas the thickness of the soluble matrix 200 in the plasma separation application illustrated in FIG. 7 needs to span the entire gap between the PSM 100 and the top of the base material 310, in the case of the metering tool CPR-Valve 200, it should be as thin as possible, such as 10-50 µm. However, unfortunately, the majority of the material comprising the CPR-Valve will be passed downstream in the liquid, (e.g. blood) and, in this application, cannot be bypassed as it is in the plasma separation application.

Microchannel Capillary Re-Set. While the example above illustrated the use of the soluble matrix to overcome a single capillary stop junction to aid in automatic metering, a related design can be used to overcome capillary stop junctions of multiple small microchannels. This is achieved by using the soluble matrix to overcome, first, a single capillary stop junction, and then using the flow generated by this process to wet-through the capillary stop junctions in following microchannels connected to the same collection channel. This is illustrated in FIG. 10.

Figure 10:
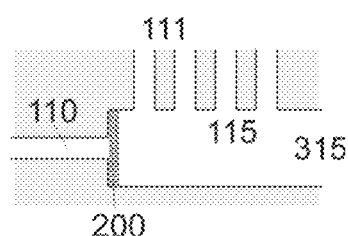
FIG. 10 illustrates a microfluidic channel embodiment of the disclosed technology where multiple small channels of high capillarity empty into a single larger channel of lower capillarity.

In FIG. 10 a CPR-Valve 200, in the form of a soluble matrix, is in physical contact with the exterior surface of a capillary stop junction of one microchannel 110. As in the previous example, this allows flow to proceed past this stop junction and into the collection channel 315. One or more additional small microchannels may also be present 111 connected to the collection channel 315. At the interface of connection of these smaller microchannels 111 to the collection channel 315, capillary stop junctions are present 115. As liquid flows through the initial channel 110 and into the collection channel 315, it will eventually flow past these stop junctions 115, allowing them to be wetted-through from the side of the collection channel 315, thus eliminating the air-liquid barrier and causing the capillary forces preventing the liquid from moving forward to disappear.

This is actually a microchannel version of what happens when a membrane is used, except rather than just a few additional microchannels and capillary stop junctions, there are many thousands depending on the nature and size of the membrane.

In FIG. 10, ideally, the liquid in the successive microchannels will already be at the stop junctions 115 before liquid in the collection channel 315 flows past them, otherwise bubbles may be trapped and further flow through the microchannels 111 will be blocked. Any number of microchannels 111 may be present depending on the needs of the application. The initial microchannel 110 can stem from the same source of the other microchannels 111, such as by branching off of them, or the liquid could come from an independent source.

Although it has been emphasized that membrane based filtration has several advantages over microchannel filtration, the design illustrated in FIG. 10 can help reduce some of the limitations of microchannel filtration, or microfluidics in general where the need for successively smaller microchannels, either for size-exclusion filtering or to drive capillary flow, may be needed. In this design, the high capillarity present in the small microchannels 110 and 111, can be re-set to a less stringent system which are, typically, easier and more economical to fabricate.

While preferred embodiments of the invention have been illustrated, it will be obvious to those skilled in the art that various modifications and changes may be made thereto without departing from the spirit and scope of the invention as hereinafter defined in the appended claims.

The invention claimed is:

1. A microchannel device comprising:
a collection channel;
a first microchannel connected to the collection channel and forming a first capillary stop junction between the first microchannel and the collection channel;
one or more second microchannels connected to the collection channel and forming one or more second capillary stop junctions between the second microchannel and the collection channel, the one or more second capillary stop junctions being downstream of the first capillary stop junction; and
a soluble matrix placed in the collection channel at the first capillary stop junction, the soluble matrix possessing a capillary drawing force sufficient to draw liquid from the first microchannel into the soluble matrix and at least partially dissolving or disintegrating in the liquid and thereby releasing the liquid into the collection channel, whereby a capillary barrier of the first stop junction is overcome, causing the liquid to flow along the collection channel and past the one or more second capillary stop junctions to thereby wet-through and overcome capillary barriers of the one or more second capillary stop junctions.

2. The microchannel device of claim 1, wherein the collection channel has a first dime tear, the first microchannel is connected to an inlet of the collection channel and has a second diameter that is smaller than the first diameter, and the soluble matrix is placed in the collection channel at the inlet.

3. The microchannel device of claim 2, wherein the one or more second microchannels are connected to the collection channel through one or more openings in a side surface of the collection channel.

4. The microchannel device of claim 1, wherein the one or more second microchannels comprise multiple second microchannels.

5. The microchannel device of claim 1, wherein the first microchannel branches off from one of the one or more second microchannels.

6. The microchannel device of claim 1, wherein the soluble matrix comprises a micro- or nano-particulate or fibrous material of at least one of a simple or complex salt, sugar, protein, carbohydrate, acid, or base.

7. A method comprising:
providing a microchannel device comprising a collection channel, a first microchannel connected to the collection channel and forming a first capillary stop junction between the first microchannel and the collection channel, one or more second microchannels connected to the collection channel and forming one or more second capillary stop junctions between the one or more second microchannels and the collection channel downstream of the first capillary stop junction, and a soluble matrix placed in the collection channel at the first capillary stop junction;
filling the one or more second microchannels with liquid, whereby one or more liquid-air barriers at the one or more second stop junctions are formed; and
filling the first microchannel with liquid, causing the liquid to be drawn by capillary forces from the first microchannel into the soluble matrix and causing the soluble matrix to at least partially dissolve or disintegrate in the liquid and thereby release the liquid into the collection channel, whereby a capillary barrier of the first stop junction is overcome, causing the liquid to flow along the collection channel and past the one or more second capillary stop junctions to thereby wet-through the one or more liquid-air barriers at the one or more second capillary stop junctions, causing the fluid filling the one or more second microchannels to proceed into the collection channel.

8. The method of claim 7, wherein the collection channel has a first dimeter, the first microchannel is connected to an inlet of the collection channel and has a second diameter that is smaller than the first diameter, and the soluble matrix is placed in the collection channel at the inlet.

9. The method of claim 8, wherein the one or more second microchannels are connected to the collection channel through one or more openings in a side surface of the collection channel.

10. The method of claim 7, wherein the one or more second microchannels comprise multiple second microchannels.

11. The method of claim 7, wherein the first microchannel branches off from one of the one or more second microchannels.

12. The method of claim 7, wherein the soluble matrix comprises a micro- or nano-particulate or fibrous material of at least one of a simple or complex salt, sugar, protein, carbohydrate, acid, or base.

13. The method of claim 7, wherein the one or more second microchannels are filled and the one or more liquid-air barriers are formed before the liquid flowing along the collection channel passes the respective one or more second capillary stop junctions.

14. A liquid sample metering device, comprising:
a capillary tube including a first section having a first diameter, a second section having a second diameter, and a third section having a third diameter, the third diameter being smaller than the first diameter, the second section being placed between the first and third sections, the capillary tube dimensioned such that, when an inlet of the first section at an end opposite to the second section is brought in contact with a source of liquid sample, the first and second sections fill with the liquid sample via capillary forces and a capillary stop junction is formed between the second and third sections; and
a soluble matrix placed in the third section at an interface with the second section, the soluble matrix possessing a capillary drawing force sufficient to draw the liquid sample into the soluble matrix, causing the soluble matrix to at least partially dissolve or disintegrate in the liquid sample and thereby release the liquid sample into the third section, whereby the capillary stop junction between the second and third sections is overcome such that, if the inlet of the first section is removed from the source of liquid sample prior to release of the liquid sample into the third section, a metered volume of the liquid sample passes into the third section.

15. The liquid sample metering device of claim 14, wherein the third diameter is greater than the second diameter, and wherein the metered volume is equal to an interior volume of the first section of the capillary tube.

16. The liquid sample metering device of claim 14, wherein a capillarity of the third section is greater than a capillarity of the second section, and wherein the metered volume is equal to a total interior volume of the first and second sections of the capillary tube.

17. The liquid sample metering device of claim 14, wherein the third section comprises a vent near the interface with the second section.

18. The liquid sample metering device of claim 14, wherein the soluble matrix comprises a micro- or nano-particulate or fibrous material of at least one of a simple or complex salt, sugar, protein, carbohydrate, acid, or base.

19. The liquid sample metering device of claim 14, wherein an average pore size of the soluble matrix is about 50 µm.

20. The liquid sample metering device of claim 14, wherein the soluble matrix has a thickness between 10 µm and 50 µm.

* * * * *